United States Patent
Smith et al.

(12) 
(10) Patent No.: US 6,565,894 B1
(45) Date of Patent: May 20, 2003

(54) HEALTHCARE FORMULATIONS COMPRISING IMIDAZOLE AND HYDROGEN PEROXIDE

(76) Inventors: Francis X. Smith, 22 Fox Run, Salem, NH (US) 03079; John Randall Tracey, 109 Shadow Lake Rd., Salem, NH (US) 03079

( * ) Notice: Subject to any disclaimer, the term of this patent is extended or adjusted under 35 U.S.C. 154(b) by 0 days.

(21) Appl. No.: 09/706,340

(22) Filed: Nov. 4, 2000

Related U.S. Application Data

(60) Provisional application No. 60/163,686, filed on Nov. 5, 1999.

(51) Int. Cl.[7] .................. A61K 33/40; A61K 31/4172; A61K 31/155
(52) U.S. Cl. ................. 424/616; 514/396; 514/399; 514/400; 514/634; 514/635; 514/912; 514/913; 514/914; 514/915
(58) Field of Search ................. 514/385–402, 514/912, 914, 915, 944, 634, 635, 913; 424/616

(56) References Cited

U.S. PATENT DOCUMENTS 5,122,354 A * 6/1992 Tsuji et al. ................. 423/272

* cited by examiner

*Primary Examiner*—John Pak
(74) *Attorney, Agent, or Firm*—Christopher E. Blank; Jaeckle Fleischmann & Mugel, LLP

(57) ABSTRACT

An ophthalmic solution comprising: 0.01 to 5 weight percent imidazole: 0.01 to 30 weight percent hydrogen peroxide and the balance water which can further comprisie 0.01 to 2 weight percent of a buffer adjusted so the pH of the formulation is between 5.5 to 8.5.

4 Claims, No Drawings

HEALTHCARE FORMULATIONS COMPRISING IMIDAZOLE AND HYDROGEN PEROXIDE

This application claims the benefit of U.S. Provisional application No. 60/163,686, filed on Nov. 05, 1999.

BACKGROUND

The present invention relates to an improved preservative system for healthcare preparations including ophthalmic solutions, topical gels, creams, rinses and other pharmaceutical applications that utilize an aqueous base and require preservation against microbial contamination. These improved compositions comprise in part a preservative package comprising imidazole and a hydrogen peroxide source. It has been found that this combination of imidazole and hydrogen peroxide have a surprising efficacy against a broad spectrum of bacteria and fungi. Typically preservative combinations known and used in the state of the art are effective against bacteria or fungi, but usually not in combination. The present invention combination preservative package is effective against both fungi and bacteria also exhibits low cytotoxicity and is therefore useful in healthcare applications where said solution is likely to be in contact with tissue in use.

It has been found that at relatively low levels of hydrogen peroxide and imidazole provide activity against both bacteria and fungi, and surprisingly this combination of components forms a preservative package that is more effective against fungi than bacteria. In the state of the art, healthcare solutions, especially ophthalmic solutions have preservative packages that are limited in the ability to control the growth of fungi. Therefore, the state of the art has resorted to higher levels of preservatives to combat this phenomena, often employing long chain quaternary amine compositions or polymeric biguinides, both of which due to their cationic nature tend to bind to the surface of contact lenses or other biomedical devices that are placed in intimate contact with tissue or bodily fluids. Therefore, it would be useful to use a broader spectrum preservative package that would be effective against both bacteria and fungi, and could be used at lower levels than previous preservatives or preservative packages. This invention is not limited to ophthalmic solutions, but is considered to be useful and include healthcare compositions that are intended to clean, preserve, or provide antibacterial or antifungal activity topically.

The present invention relates to an improved preservative package comprised of imidazole, or an imadazole analog and hydrogen peroxide. This preservative package may be used in health care formulation to be applied topically, including ophthalmic care solutions including solutions used ophthalmologically and in contact lens care applications. Specifically in ophthalmic applications, the solutions comprise 0.1 to 5 weight percent of the imidazole or imidazole analog and 5 to 130,000 ppm hydrogen peroxide. These ophthalmic solutions may also include buffering agents, tonicity agents, preservatives, wetting agent, demulcents, surfactants and active pharmaceutical agents as well as the preservative package.

Typically, the imidazole is present at 0.01 to 5weight percent; preferably 0.1 to 0.5 weight percent. The imidazole analogs may chosen from the group consisting of imidazole; bifonazole, butoconazole, chlordantoin, chloroimidazole, cloconazole, clotrimazole, econazole, enilconazole, fenticonazole, flutrimazole, isocanazole, ketocanazole, lanoconazole, miconazole, omoconazole, oxiconazole, sertaconazole, sulconazole, and tioconazole, all of which are known in the art.

Buffering Agents

The buffer component which is present in an amount effective to maintain the pH of the liquid medium in the desired range. Among the suitable buffer components or buffering agents which may be employed are those which are conventionally used in contact lens care products. Examples of useful buffer components include those with carbonate functionalities, bicarbonate functionalities, phosphate functionalities, borate functionalities, organic amines, and the like and mixtures thereof The buffers may be alkali metal and alkaline earth metal salts, in particular sodium and potassium chloride.

Tonicity Agents

In order to avoid possible eye irritation, ophthalmic solutions made according to the invention should have an osmolality (a measure of tonicity) of at least about 200 mOsm/kg, preferably in the range of about 200 to about 400 or about 300 mOsm/kg. In an especially useful embodiment, the osmolality or tonicity of the combined liquid medium substantially corresponds to the tonicity of the fluids of the eye, in particularly the human eye.

Any suitable ophthalmically acceptable tonicity component or components may be employed, provided that such component or components are compatible with the other ingredients of the combined liquid medium and do not have deleterious or toxic properties which could harm the eye. Examples of useful tonicity components include sodium chloride, potassium chloride, mannitol, dextrose, glycerin, propylene glycol and mixtures thereof. In one embodiment, the tonicity component is selected from inorganic salts and mixtures thereof. It is preferred that the tonicity of the ophthalmic solutions not depend upon sodium chloride to the extent possible.

The amount of ophthalmically acceptable tonicity component utilized can vary widely. In one embodiment, the tonicity component is preferably present in the combined liquid medium in an amount in the range of about 0.1 to about 0.9% w/v of the combined liquid medium.

Other Agents

Examples of such additional components include cleaning agents, wetting agents, nutrient agents, sequestering agents, viscosity builders, contact lens conditioning agents, colorants, and the like. These additional components may each be included in the combined liquid medium in an amount effective to impart or provide the beneficial or desired property to the combined liquid medium. Such additional components may be included in the presently useful liquid media in amounts similar to the amounts of such components used in other, e.g., conventional, contact lens care products.

Examples of useful sequestering agents include disodium ethylene diamine tetraacetate, alkali metal hexametaphosphate, citric acid, sodium citrate and mixtures thereof Viscosity builders include hydroxyethyl cellulose, hydroxymethyl cellulose, polyvinyl pyrrolidone, polyvinyl alcohol and mixtures thereof

Enzymes

The present invention may also further include enzymes useful in cleaning contact lenses. These enzymes include, but are not necessarily limited to, peroxide-active enzymes which are conventionally employed in the enzymatic cleaning of contact lenses. For example, many of the enzymes disclosed in Huth et al U.S. Reissue Pat. No. 32,672 and Karageozian et al U.S. Pat. No. 3,910,296 are useful in the present invention. These patents are incorporated in their entirety by reference herein. Among the useful enzymes are those selected from proteolytic enzymes, lipases and mixtures thereof Preferred proteolytic enzymes are those which are substantially free of sulfhydryl groups or disulfide bonds, whose presence may react with the active oxygen in the HPLM to the detriment of the activity of the enzyme. Metallo-proteases, those enzymes which contain a divalent metal ion such as calcium, magnesium or zinc bound to the protein, may also be used.

DETAILED DESCRIPTION

EXAMPLE 1

Experiment BCL075-126
Protein Stability

Test solutions were prepared according to the formulas indicated in the table had undenatured protein added in a control and were heated to approximately 80 degrees Celsius as indicated. Each sample was observed for clarity. This test provides useful results for indicating the protein is stabilized in comparison with other solutions subjected to the same test regimen.

lenses were rinsed with distilled water in order to remove residual solution. The lenses were then assayed for protein deposition using a Beckman BioGamma 1 counter. Results were reported in ug/lens.

|  | Lens A µg/lens | Lens B µg/lens | Average µg/lens |
|---|---|---|---|
| Phosphate buffer control | 1,043 | 865 | 954 |
| 1% Imidazole - hydrogen peroxide | 64 | 13 | 38.5 |

The test solution was 1% imidazole and 60 ppm hydrogen peroxide in phosphate buffer. The matrix control was phosphate buffer and sodium chloride. The imidazole-hydrogen peroxide solution had lower protein binding than the control.

EXAMPLE 3

Experiment BCL058-198
Example of Protein Deposition Inhibition

Isotonic aqueous phosphate buffered solutions were prepared and adjusted to pH 7.4. Contact lenses were soaked in

| | | | | | Weight | | | | |
|---|---|---|---|---|---|---|---|---|---|
| Solution | 10 80° C. 15 min | 8 80° C. 30 min | 7 80° C. 45 min | 6 80° C. 60 min | 4 Ambient 15 min | 3 Ambient 30 min | 2 Ambient 24 hour | 1 Ambient 48 hour | Total |
| A | 0 | 0 | 0 | 1 | 2 | 2 | 3 | 3 | 29 |
| B | 0 | 0 | 0 | 0 | 1 | 1 | 2 | 3 | 14 |
| C | 1 | 2 | 3 | 3 | 3 | 3 | 3 | 3 | 95 |
| D | 3 | 3 | 3 | 3 | 3 | 3 | 3 | 3 | 123 |
| E | 0 | 1 | 3 | 3 | 3 | 3 | 3 | 3 | 77 |
| F | 1 | 3 | 3 | 3 | 3 | 3 | 3 | 3 | 103 |
| G | 1 | 3 | 3 | 3 | 3 | 3 | 3 | 3 | 103 |

A. 1% Imidazole in phosphate buffer
B. 1% Imidazole with 60 ppm hydrogen peroxide in phosphate buffer
C. phosphate buffer control
D. marketed product having the general composition: A sterile, aqueous, buffered, slightly hypertonic solution containing PEO sorbitan monolaurate and a betaine surfactant as cleaning agents; a slilicone glycol copolymer, a cellulosic viscosifier preserved with chlorhexidine gluconate (0.003%), polyaminopropyl biquanide (0.0005% and edetate disodium (0.05%).
E. marketed product having the general composition: A sterile, isotonic solution that contains boric acid, edetate disodium, poloxamine, sodium borate and sodium chloride; preserved with DYMED (polyaminopropyl biquanide) 0.00005%.
F. marketed product having the general composition: A sterile, isotonic solution that contains HYDRANATE (hydroxyalkylphosphonate), boric acid, edetate disodium, poloxamine, sodium borate and sodium chloride; preserved with DYMED (polyaminopropyl biquanide) 0.0001%.
G. marketed product having the general composition: A sterile isotonic aqueous solution containing sodium chloride, polyoxyethylene polyoxypropylene block copolymer, sodium phosphate dibasic, sodium phosphate monobasic, and preserved with edetate disodium dihydrate 0.025% and polyhexanide 0.0001%.

A weighting factor as indicated in the table was used to multiply each result. 0 indicated a clear sample; 1 slightly turbid, 2 turbid, and 3 indicated cloudy and separate phases (precipitate). The data illustrates the synergistic ability of hydrogen peroxide with imidazole to stabilize the protein and thus decrease the extent of opacification on the contact lens from the protein deposit. Both formulas performed superior to the marketed product.

EXAMPLE 2

Experiment BCL058-198
Example of Protein Deposition Inhibition

Contact lenses were soaked and heated in test solutions to which a radio-labeled lysozyme was present in a known amount for a period of 12 hours at 37 degrees Celsius. The 25 mL of the test solutions overnight. Afterwards, lysozyme was added to the tubes and warmed to 37 degrees Celsius for 12 hours. The lenses were rinsed with distilled water in order to remove residual solution. The lenses were assayed for protein deposition by the BCA method and detected on an HP PDA Spectrophotometer. Results were reported in ug/lens.

| Solution | µg lysozyme per lens |
|---|---|
| Marketed Product Control (phosphate buffer, Poloxamer) | >18.3 |

| Solution | μg lysozyme per lens |
|---|---|
| Phosphate buffer control | >26.16 |
| 1% Imidazole - hydrogen peroxide | 4.87 |

The matrix control was phosphate buffer and sodium chloride. The imidazole-hydrogen peroxide solution had lower protein binding than the control.

EXAMPLE 4

An aqueous solution containing imidazole (1.5%), hydrogen peroxide (60 ppm), Pluronic F127 (0.1%), glycerin (0.5%) was prepared the pH was adjusted to pH 7.37.

Polyhexamethylene biquanide (PHMB) was added to half of this solution to yield a final concentration of 1 ppm. An second set of aqueous solution containing imidazole (1.5%), Pluronic F127 (0.1%), glycerin (0.5%) was prepared the pH was adjusted to pH 7.35. Polyhexamethylene biquanide (PHMB) was added to half of this solution to yield a final concentration of 1 ppm. A third set of aqueous solutions containing Pluronic F127 (0.1%) and glycerin (2%) was prepared the pH was adjusted to pH 7.65. Polyhexamethylene biquanide (PHMB) was added to half of this solution to yield a final concentration of 1 ppm. A fourth set of aqueous solutions containing hydrogen peroxide (60 ppm), Pluronic F127 (0.1%) and glycerin (2.3%) was prepared the pH was adjusted to pH 7.35. Polyhexamethylene biquanide (PHMB) was added to half of this solution to yield a final concentration of 1 ppm.

Each of these solutions were tested for their activity against *S. aureus* and *C. albicans*. The data are summarized in the following table.

| Formulation | *S. aureus* 4 hours | *C. albicans* 4 hours |
|---|---|---|
| Imidazole, Hydrogen Peroxide | 0.77 | >4.74 |
| Imidazole, Hydrogen Peroxide, PHMB | 4.03 | >4.74 |
| Imidazole | 0.26 | 0.01 |
| Imidazole, PHMB | >4.73 | 1.28 |

The results of this analysis indicates the effect of pH on the ability to disinfect the solution against *C. albicans*.

EXAMPLE 5

The following examples illustrate various formulations that have been made according to the present invention. These examples are meant to be illustrative rather than exhaustive and do not delineate the scope of the presently claimed invention. Formulation of the aqueous based examples involves practices well known and understood in the art and it is not thought the method of manufacture effect the compositions made according to the following examples as long as adequate care is taken to minimize microbial contamination.

Aqueous solutions were prepared according to the following table

|  | Formulation 1 | Formulation 2 | Formulation 3 |
|---|---|---|---|
| Choline Chloride | none | none | 0.50% |
| Imidazole | 0.75% | 1.00% | 1.00% |
| Diethylenetriaminepenta-(methylenephosphonic acid) (Dequest 2060S) | 60 ppm | 60 ppm | 60 ppm |
| Ethoxylated castor oil (Cremophor RH 40) | 0.10% | 0.10% | 0.10% |
| Hydrogen Peroxide | 40 ppm | 60 ppm | 40 ppm |
| Polyhexamethylenebiquanide (Cosmocil CQ) | 1 ppm | 1 ppm | 1 ppm |
| Sodium Chloride | Osm Adj | Osm Adj | Osm Adj |
| Hydrochloric Acid | pH adj | pH adj | pH adj |
| Sodium Hydroxide | pH adj | pH adj | pH adj |
| pH | 7.3 | 7.3 | 7.3 |
| Osmolality | 300 mOsm | 300 mOsm | 300 mOsm |

EXAMPLE 6

The following solution is an example of a gel that can be prepared.

| Ingredients | Percent w/v |
|---|---|
| Carbomer* tm | 0.5 |
| Imidazole | 0.3 |
| Hydrogen Peroxide, USP | 0.3 |
| Water | dilute to 100 ml |

*Carbomer is a viscosity increasing agent

| | | |
|---|---|---|
| No preservative | 0.05 | −0.09 |
| PHMB | 4.03 | 2.40 |
| Hydrogen peroxide | 1.95 | 1.06 |
| Hydrogen peroxide, PHMB | >4.73 | 3.08 |
| Marketed Product 1 * | >4.73 | 0.54 |
| Marketed Product 2 ** | >4.73 | 2.57 |

* marketed product 1 having the general composition: A sterile isotonic aqueous solution containing sodium chloride, polyoxyethylene polyoxypropylene block copolymer, sodium phosphate dibasic, sodium phosphate monobasic, and preserved with edetate disodium dihydrate 0.025% and polyhexanide 0.0001%.
** marketed product 2 having the general composition: A sterile, isotonic solution that contains HYDRANATE (hydroxyalkylphosphonate), boric acid, edetate disodium, poloxamine, sodium borate and sodium chloride; preserved with DYMED (polyaminopropyl biquanide) 0.0001%.

The results demonstrate the selectivity of the imidazole-hydrogen peroxide combination against *C. albicans*. Even without the supplemental preservative, the effectiveness was superior to that found in either commercially marketed products.

EXAMPLE 7

The Effect of pH on the Efficacy Against *C. albicans*

Into a calibrated polypropylene, 375 mL of purified water was measured. Five grams of imidazole, 3.0 mL hydrogen peroxide (3%) and 1.25 g choline chloride was added to the water and mixed for 15 minutes. A second phase was prepared by adding 5 g glycerin to 50 g water heated to 60° C. Cremophor RH 40 (0.5 g) previously heated to 60° C. was transferred into a beaker and placed on a hot plate. The second phase solution was transferred to this solution and mixed. All phases were combined at room temperature and diluted to 500 mL with purified water. Following this, 5.0 mL polyhexamethylene biquanide (0.1 mg/mL) was added and mixed well. This final solution was divided into 10 separate tubes and the pH adjusted as indicated in the following table. Each of these solutions were tested against *C. albicans* and the log reduction after two hours was determined. The results of this test are tabulated below.

| pH | *C. albicans* Log Reduction |
| --- | --- |
| 2.92 | 0.56 |
| 5.95 | 0.82 |
| 6.37 | 0.84 |
| 6.66 | 1.16 |
| 6.97 | 2.12 |
| 7.25 | 3.29 |
| 7.55 | 4.29 |
| 8.11 | 4.76 |
| 8.41 | 4.76 |
| 9.66 | 4.76 |

What is claimed is:

1. An ophthalmic solution comprising:

5 to 130,000 ppm hydrogen peroxide;

0.01 to 5 weight % histidine;

the balance water.

2. The ophthalmic solution of claim 1 further comprising an effective amount of a physiologically effective buffer adjusted to a pH between 6.5 and 8.5.

3. The ophthalmic solution of claim 1 further comprising an effective amount of a cationic preservative.

4. The ophthalmic solution of claim 1 further comprising about 1 part per million PHMB.

* * * * *